US011034929B2

(12) United States Patent
Cannon et al.

(10) Patent No.: US 11,034,929 B2
(45) Date of Patent: Jun. 15, 2021

(54) INSTRUMENT RESOURCE SCHEDULING

(71) Applicant: Thrive Bioscience, Inc., Wakefield, MA (US)

(72) Inventors: Howard Cannon, Boston, MA (US); Keith Moulton, Amesbury, MA (US)

(73) Assignee: Thrive Bioscience, Inc., Wakefield, MA (US)

( * ) Notice: Subject to any disclaimer, the term of this patent is extended or adjusted under 35 U.S.C. 154(b) by 343 days.

(21) Appl. No.: 15/776,774

(22) PCT Filed: Nov. 18, 2016

(86) PCT No.: PCT/US2016/062725
§ 371 (c)(1),
(2) Date: May 16, 2018

(87) PCT Pub. No.: WO2017/087774
PCT Pub. Date: May 26, 2017

(65) Prior Publication Data
US 2018/0327708 A1 Nov. 15, 2018

Related U.S. Application Data

(60) Provisional application No. 62/257,196, filed on Nov. 18, 2015.

(51) Int. Cl.
*C12M 1/36* (2006.01)
*C12M 1/00* (2006.01)
(Continued)

(52) U.S. Cl.
CPC ............ *C12M 41/48* (2013.01); *C12M 41/14* (2013.01); *G06F 9/50* (2013.01); *G06F 9/5005* (2013.01); *G06N 7/00* (2013.01)

(58) Field of Classification Search
CPC .......... H04L 41/0213; H04L 29/08072; H04L 29/06; H04L 41/22; H04L 41/12; C12M 41/48; C12M 41/14; G06N 7/00
(Continued)

(56) References Cited

U.S. PATENT DOCUMENTS 7,267,795 B2 * 9/2007 Ammann ............. G01N 35/025
422/63
10,287,548 B2 * 5/2019 Keskar ..................... G01N 3/08
(Continued)

OTHER PUBLICATIONS

Petronis et al. ("Transparent polymeric cell culture chip with integrated temperature control and uniform media perfusion", BioTechniques, 2006, pp. 368-375) (Year: 2006).*
(Continued)

*Primary Examiner* — Iftekhar A Khan
(74) *Attorney, Agent, or Firm* — Danielson Legal LLC

(57) ABSTRACT

Aspects of the present invention relate to an automated cell culture instrument and to methods for operating such an instrument. In one aspect, the cell culture instrument includes a computing unit and a plurality of electrically controllable resources (e.g., sensors, actuators, etc.). The computing unit receives a protocol, schedules the resources so as to execute the protocol, and operates the resources as scheduled or in response to so as to provide an improved environment for cell culture growth. The computing unit may simulate protocol execution in connection with the scheduling or execution of the protocol.

20 Claims, 10 Drawing Sheets

(51) Int. Cl.
*G06F 9/50* (2006.01)
*G06N 7/00* (2006.01)
(58) Field of Classification Search
USPC .......................................................... 703/13
See application file for complete search history.

(56) References Cited

U.S. PATENT DOCUMENTS

| | | | | |
|---|---|---|---|---|
| 2005/0054083 A1* | 3/2005 | Vuong | ................ | G01N 35/028 |
| | | | | 435/287.2 |
| 2005/0054101 A1* | 3/2005 | Felder | .................... | C12M 25/14 |
| | | | | 435/383 |
| 2005/0170491 A1* | 8/2005 | Takagi | .................. | C12M 37/00 |
| | | | | 435/287.1 |
| 2005/0227243 A1* | 10/2005 | Deak | ................ | G01N 33/57484 |
| | | | | 435/6.16 |
| 2005/0239196 A1* | 10/2005 | Yanai | .................... | C12M 23/26 |
| | | | | 435/289.1 |
| 2005/0255445 A1* | 11/2005 | Van Damme | ...... | G01N 33/5008 |
| | | | | 435/4 |
| 2005/0260743 A1* | 11/2005 | Drake | .................... | C12M 41/48 |
| | | | | 435/289.1 |
| 2006/0115893 A1* | 6/2006 | Kobayashi | ............. | C12M 23/04 |
| | | | | 435/305.2 |
| 2006/0257999 A1* | 11/2006 | Chang | .................... | C40B 60/06 |
| | | | | 435/289.1 |
| 2007/0225597 A1* | 9/2007 | Banes | .................... | G06T 7/0012 |
| | | | | 600/425 |
| 2008/0317324 A1* | 12/2008 | Eblenkamp | .......... | G01N 15/147 |
| | | | | 382/133 |
| 2009/0215104 A1* | 8/2009 | Taboas | .................. | C12M 35/02 |
| | | | | 435/29 |
| 2010/0129789 A1* | 5/2010 | Self | .......................... | B01L 9/06 |
| | | | | 435/5 |
| 2010/0304472 A1* | 12/2010 | Kim | ....................... | C12M 23/38 |
| | | | | 435/304.1 |
| 2011/0136225 A1* | 6/2011 | Vunjak-Novakovic | ...................... | |
| | | | | C12M 23/46 |
| | | | | 435/325 |
| 2011/0207209 A1* | 8/2011 | Hammons | ............... | C12M 23/42 |
| | | | | 435/297.1 |
| 2012/0035742 A1* | 2/2012 | Vunjak-Novakovic | ...................... | |
| | | | | A61F 2/28 |
| | | | | 623/23.61 |
| 2012/0214189 A1* | 8/2012 | Shuler | .................... | C12M 41/48 |
| | | | | 435/29 |
| 2013/0130311 A1* | 5/2013 | Shapiro | .................... | C12Q 1/06 |
| | | | | 435/39 |
| 2014/0038257 A1* | 2/2014 | Subramanian | ........... | A61N 7/00 |
| | | | | 435/173.8 |
| 2014/0106386 A1* | 4/2014 | Umeno | .................. | B25J 9/0087 |
| | | | | 435/23 |
| 2014/0271571 A1* | 9/2014 | Magnant | ............... | C12M 41/12 |
| | | | | 424/93.7 |
| 2015/0010898 A1 | 1/2015 | Ng | | |
| 2015/0134315 A1* | 5/2015 | Sarmiento | .............. | G16B 35/20 |
| | | | | 703/11 |
| 2016/0032396 A1* | 2/2016 | Diehn | .................... | G16B 30/00 |
| | | | | 506/2 |
| 2017/0130189 A1* | 5/2017 | Sakamoto | .............. | C12M 33/10 |
| 2017/0166948 A1* | 6/2017 | Matsumoto | ............ | C12M 41/46 |
| 2017/0369833 A1* | 12/2017 | Kamiya | .................... | B25J 21/00 |
| 2018/0072980 A1* | 3/2018 | Koike | ........................ | C12N 5/06 |
| 2018/0101643 A1* | 4/2018 | Spahn | .................... | G16C 20/60 |
| 2018/0327708 A1* | 11/2018 | Cannon | ................. | G06F 9/5005 |
| 2019/0033819 A1* | 1/2019 | Chao | ....................... | G06F 9/455 |
| 2019/0119621 A1* | 4/2019 | Koike | .................... | G06T 7/0012 |

OTHER PUBLICATIONS

Triaud et al. ("Evaluation of Automated Cell Culture Incubators", The Association for Laboratory Automation, 2003, pp. 82-86) (Year: 2003).*
International Search Report for PCT/US2016/062725, dated Mar. 2, 2017, 2 pages.
Written Opinion for PCT/US2016/062725, dated Mar. 2, 2017, 6 pages.

* cited by examiner

INSTRUMENT RESOURCE SCHEDULING

CROSS-REFERENCE TO RELATED APPLICATIONS

The present application is the national phase of International (PCT) Patent Application No. PCT/US2016/062725, filed internationally on Nov. 18, 2016, and claims priority to and the benefit of U.S. provisional application No. 62/257,196 filed on Nov. 18, 2015, and is related to U.S. provisional applications No. 62/141,183, filed on Mar. 31, 2015; 62/141,187, filed on Mar. 31, 2015; 62/141,191, filed on Mar. 31, 2015; and 62/141,196, filed on Mar. 31, 2015, the entire disclosure of each of which is hereby incorporated by reference as if set forth in its entirety herein.

FIELD

Embodiments of the present invention relate generally to instruments such as incubators, and in particular to cell culture incubators with electrically-controllable resources.

BACKGROUND

Cell culture incubators are used to grow and maintain cells from cell culture, which is the process by which cells are grown under controlled conditions. Cell culture vessels containing cells are stored within the incubator, which maintains conditions such as temperature and gas mixture that are suitable for cell growth.

Long-term cell culture is a useful technique in both research and clinical contexts. However, maintenance of long-term cell cultures, for example, long term cultures, tissue preparations, in vitro fertilization preparations, etc., in presently available cell incubators is a laborious process requiring highly trained personnel and stringent aseptic conditions. This high level of human involvement can introduce contaminants into the culture and cause shock from environmental changes, thereby lowering culture efficiency.

Accordingly, new types of cell culture incubators that provide a culture system with minimal human involvement are needed.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Conventional cell culture incubators impose several barriers to productive long-term cell culture, particularly for purposes of maintaining cells for clinical purposes or for research purposes involving sensitive assays, e.g., for evaluating drug function or interrogating cellular function. For example, many presently available cell incubators require extensive operator interaction to load and unload culture plates, to move cell culture vessels, to supply sterilization medium, etc. Unfortunately, human operators introduce the possibility of human error, contamination, etc. Thus, the disclosure in part relates to a cell culture incubator that reduces human error by including one or more electrically controllable resources.

According to one aspect of the disclosure, embodiments of the present invention relate to an instrument. The instrument includes a plurality of electrically controllable resources, a processor; and a non-transitory computer-readable medium having instructions stored thereon that define at least one protocol and that, when executed by the processor, enable the processor to: receive data regarding at least one protocol to be performed by the instrument; generate a schedule regarding operation of at least one of the plurality of electrically controllable resources to perform the at least one protocol; and control at least one of the plurality of electrically controllable resources in accordance with the generated schedule of the plurality of electrically controllable resources.

In one embodiment, the plurality of electrically controllable resources include at least one of an electrically controllable device for handling a liquid medium, an electrically controllable sensor for detecting conditions in a liquid medium, an electrically controllable transfer device for moving one or more items in and out of at least one internal chamber, and an electrically controllable cell culture vessel transfer device for moving at least one cell culture vessel within the internal chamber.

In one embodiment, the instructions include at least one conditional action that specifies activation of at least one electrically controllable resource in response to a satisfied condition.

In one embodiment, the instructions include at least one range-bound conditional action specifying the activation of at least one electrically controllable resource in response to a condition falling within a predetermined range.

In one embodiment, the instructions include at least one self-modifying conditional action changing at least one of the actions specified by the conditional action or the condition of the conditional action in response to data received by the processor. In some embodiments, the condition comprises at least one of a cell type and an action performed by at least one electrically controllable resource. In one embodiment, the data is selected from the group consisting of a sensor input and a user input.

In one embodiment, the instructions provide for rescheduling a previously scheduled operation of at least one of said plurality of electrically controllable resources. In one embodiment, the instructions provide for rescheduling a previously scheduled operation in response to at least one of a material shortage and a user action.

In one embodiment, the instructions provide for monitoring the output of at least one sensor. In one embodiment, the at least one condition relates to the output of at least one sensor.

In one embodiment, the incubator further includes at least one user input device, and the instructions provide for receiving an input from said at least one user input device. In one embodiment, at least one condition relates to input received from the at least one user input device.

In one embodiment, the instructions provide for simulating the scheduled operation of at least one of said plurality of electrically controllable resources. In one embodiment, the instructions for scheduling operation utilize the results of the simulation to schedule the operation of at least one of said plurality of electrically controllable resources. In one embodiment, the simulation of the scheduled operation utilizes at least one of Monte Carlo simulations and non-stochastic simulations.

In one embodiment, the instructions for scheduling operation utilize at least one of scheduling algorithms and scheduling heuristics selected from the group consisting of task priority heuristics, task duration heuristics, improvement heuristics, and approximate solution-based heuristics.

According to another aspect of the disclosure, embodiments of the present invention relate to a networked instrument system. The system includes a database; a plurality of instruments in operable communication with the database, wherein each of the plurality of instruments includes a plurality of electrically controllable resources, a processor, and a non-transitory computer-readable medium having instructions stored thereon that define at least one protocol and that when executed by the processor, enable the processor to: receive data regarding at least one protocol to be performed by the instrument, generate a schedule regarding operation of at least one of the plurality of electrically controllable resources to perform the at least one protocol, and control at least one of the plurality of electrically controllable resources in accordance with the generated schedule of the plurality of electrically controllable resources; and a global scheduling device in operable communication with the database and including a processor and a non-transitory computer-readable medium having instructions stored thereon that when executed by the processor generate a schedule of at least one protocol to be executed by at least one of the plurality of instruments.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
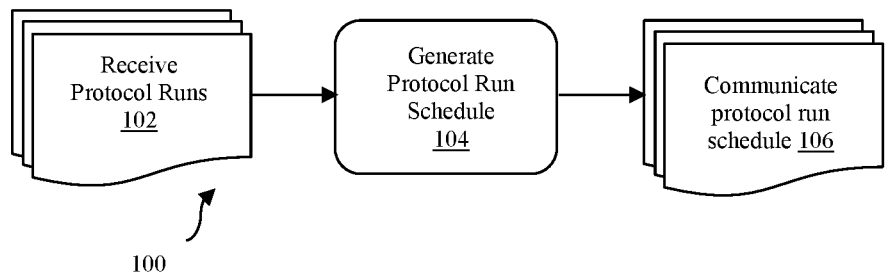
FIG. 1 depicts a flowchart of a method of globally scheduling protocols in accordance with one embodiment.

Aspects of the disclosure relate to automated incubators that enable productive long-term cell culture. It has been appreciated that, since traditional cell culture incubators require significant amounts of human intervention, the traditional incubation process is subject to myriad sources of error that can disrupt culture growth. For example, the mistaken introduction of items into an incubator by an operator from the external environment at the incorrect time or the incorrect stage of the incubation process can negatively affect the health or activity of a sample. Similarly, an operator's failure to follow the timing or order of steps specified by a protocol can kill a culture outright or invalidate the results of the culturing process.

According to one aspect, a cell culture incubator is equipped with a computing unit and one or more electrically controllable resources. These incubators may include a variety of such components, such as but not limited to sensors, environmental control systems, fluidics transport systems, robotics, etc., which may operate together at the direction of a computer, processor, microcontroller or other computing device. The computing unit controls the cell culture incubator and automatically schedules commands for execution by the components, monitors and adjusts cell culture conditions for optimal growth of the cell culture.

The computing unit can be programmed with a variety of protocols stored in a non-transitory storage medium. Each protocol describes how the computing unit should operate the electrically controllable resources to incubate a particular cell line or culture. Each individual protocol will have its own duration, which may itself vary during execution, depending on the protocol's purpose.

In the context of the present application, the term "protocol" may refer to a sequential list of parameterized procedures. Exemplary protocols may include, but are not limited to, measuring confluence or changing a particular media.

Each protocol may include a variety of conditional actions, i.e., actions triggered upon the satisfaction of a particular condition. Examples of such conditions include, but are not limited to, a value meeting a particular value or falling within a particular range, the result of an automated or semi-automated analytical technique (e.g., image analysis, pH measurement, etc.), the result of a command received via a user interface from an operator, etc. In various embodiments particular values of interest include absolute time, relative time, elapsed time, etc. The threshold values or ranges of interest may be programmed in advance or derived in an automated manner from various data sets, such as previous runs of the protocol currently being executed, or other protocols executed in connection with the particular cell type of interest. Examples of such actions may include the operation of a particular piece of electrically controllable equipment or the execution of another protocol, such as a sub-protocol or a replacement protocol.

In various embodiments, a human operator or a computing unit may alter the stored protocol to address various operating conditions or constraints. As the computing unit processes the protocol, it may schedule various electrically controllable resources so as to execute the protocol. In various embodiments the scheduler accounts for the capabilities of a particular incubator, including limited supplies of consumables, the dependency of later operations on the successful completion of early operations, the ability of the incubator to perform certain operations in parallel, the scheduled use of the incubator resources (e.g., transport resources) by another protocol, etc.

In the context of the present application, the term "procedure" may refer to a step of a protocol. Exemplary procedures may include, but are not limited to, transferring liquid, rocking a plate, triturating steps, acquiring images, and monitoring cells.

In the context of the present application, the terms "protocol run" may refer to a particular instance of a protocol. A protocol run may be defined by user specified parameter values for one or more procedures.

In the context of the present application, the term "command" may refer to a single task that can be executed by a device (e.g., a motor, pump, camera, etc.). Exemplary commands may include, but are not limited to, aspirate, dispense, MoveToWell, and EjectTip.

In the context of the present application, the terms "incubator" or "cell culture incubator" may refer to any type of instrument that may be used to at least assist in cell culture growth, development, monitoring, analysis, or the like. These instruments may also be used to perform any one of various tests on cell cultures.

FIG. 1 depicts a flowchart of a method 100 of globally scheduling protocols in accordance with one embodiment. As mentioned above a "protocol" may refer to a sequential list of parameterized procedures. These may be to measure the number of cells (confluence) every 8 hours, change media every 24 hours, passage when confluence is greater or equal to some threshold (e.g., 80%), or the like.

Step 102 of method 100 involves receiving one or more protocol run assignments. The protocol runs may be communicated by an operator, for example. The protocol run assignments may also include data regarding recurrence rules. The data regarding the protocol runs and recurrence rules may be communicated to a global scheduler module in communication with a plurality of incubator devices.

Figure 2:
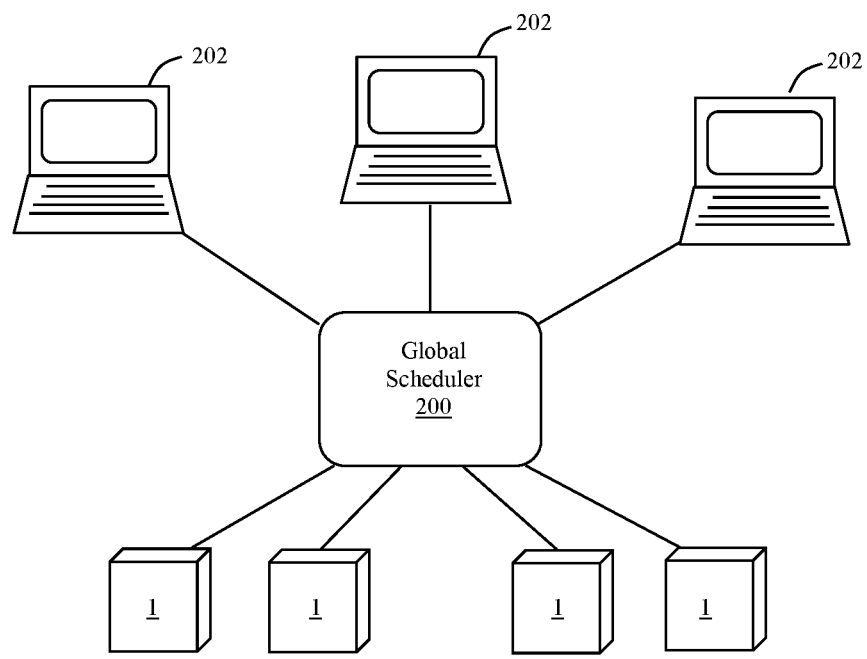
FIG. 2 illustrates a system for globally scheduling protocols in accordance with one embodiment.

For example, FIG. 2 generally illustrates a global scheduler module 200 in operable communication with a plurality of interfaces 202. Each of the interfaces 202 may be configured as a laptop, PCs, tablet, mobile device, smartwatch, or the like. The exact configuration of the interfaces 202 may vary as long as they can at least communicate data regarding protocols to the global scheduler module 200. The interfaces 202 and the global scheduler module 200 may be connected via any type of wired or wireless connection.

Step 104 involves generating a protocol run schedule. The global scheduler module 200 may assess existing protocols being run by each incubator 1, the capabilities of each incubator 1, available resources at each incubator 1, or any other type of data regarding the operation of the incubators 1, as well as any specific instructions inputted by an operator.

Step 106 involves communicating the protocol run schedule to one or more incubators 1. These schedules may be received by the incubators 1 via their interfaces. The incubators 1 may then analyze the assigned protocol to determine how to best execute the protocol as discussed below. Accordingly, the schedules may be a hierarchy of schedules that span several networked incubators 1. The incubators 1 may include a variety of electrically controllable resources to carry out the required commands.

The electrically controllable resources may include in various embodiments, for example, a transfer device (e.g., robotic arm, a conveyor belt, etc.), a liquid handling device (e.g., a pump), a delivery system for delivering culture vessels or other components to or from the incubator, an environmental control system for controlling the temperature, humidity, barometric pressure, and other environmental aspects of the incubator, a door operation system, an imaging or detection system, and a cell culture assay system.

In various embodiments each of these resources can be associated with an incubator (e.g., fitted within an incubator cabinet), incorporated as part of an incubator (e.g., attached to, integral to, or otherwise connected to an internal wall or door of an incubator), or positioned at a suitable location(s) outside or inside an incubator cabinet (e.g., within a transfer chamber and/or an internal chamber, for example attached to an internal wall, and/or upper or lower internal surface).

In various embodiments, control of the operations of a cell culture incubator and/or components provided therein or interfacing therewith may be implemented using hardware, software, or a combination thereof. When implemented in software, the software code can be executed on any suitable processor or collection of processors, whether provided in a single computing unit or distributed among multiple computing units. Such processors may be implemented as integrated circuits, with one or more processors in an integrated circuit component. A processor may be implemented using circuitry in any suitable format. A typical processor is an x86, x86-64, ARMv7 processor, and the like.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a non-volatile computer memory, one or more floppy discs, compact discs (CD), optical discs, digital versatile disks (DVD), magnetic tapes, flash memories, circuit configurations in Field Programmable Gate Arrays or other semiconductor devices, or other tangible storage medium) encoded with one or more programs that, when executed on one or more computing units or other processors, perform methods that implement the various methods or processes described herein.

In various embodiments, a computer readable storage medium may retain information for a sufficient time to provide computer-executable instructions in a non-transitory form. Such a computer readable storage medium or media can be transportable, such that the program or programs stored thereon can be loaded onto one or more different computing units or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computing unit or other processor to implement various aspects of the methods or processes described herein. Additionally, it should be appreciated that according to one aspect of this embodiment, one or more programs that when executed perform a method or process described herein need not reside on a single computing unit or processor, but may be distributed in a modular fashion amongst a number of different computing units or processors to implement various procedures or operations.

Executable instructions may be in many forms, such as program modules, executed by one or more computing units or other devices. Generally, program modules include routines, programs, objects, components, data structures, etc., that perform particular tasks or implement particular abstract data types. Typically, the functionality of the program modules may be organized as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, located within the incubator but outside the incubator cabinet, located in proximity to the incubator and in electrical communication with the incubator or an associated computing unit, etc.), and can be stored in computer-readable media to provide information about conditions during a cell culture incubation. In some embodiments, the computer-readable media comprises a database. In some embodiments, said database contains data from a single incubator. In some embodiments, said database contains data from a plurality of incubators. In some embodiments, data is stored subject to various security mechanisms and protocols that render it resistant to unauthorized access and manipulation. In some embodiments, all data generated by the incubator(s) and related facilities are stored. In some embodiments, a subset of that data is stored.

In various embodiments, the computing unit (e.g., a computer) of a particular incubator schedules and controls various processes performed inside the incubator. For example, the computing unit may issue various signals controlling the operation or the state of various electrically-controllable resources contained in or in communication with the incubator (e.g., a manipulator, an imager, a fluid handling system, etc.). In some embodiments, the computing unit controls imaging of cell cultures, picking of cells, weeding of cells (e.g., removal of cell clumps), monitoring of cell culture conditions, adjustment of cell culture conditions, and tracking of cell culture vessel movement within the incubator.

In various embodiments, the electrically controllable resources of the incubator include, but are not limited to, one or more airlocks, doors, locks, interlocks, sterilizing means (e.g., $O_3$ generators, HO generators, heat, radiation, etc.), light sources, environmental control systems (controlling temperature, humidity, atmospheric gas composition, etc.), imaging systems (cameras, microscopes, holographic imagers, etc.), sensors (temperature, air purity, contaminant levels, pH, humidity, $N_2$, $CO_2$, $O_2$, $O_3$, HO, CO, light, meters, etc.), monitoring systems (oxygen monitors, carbon dioxide monitors, ozone gas detectors, hydrogen peroxide monitors, multi-gas monitors, etc.), filtration systems (fluid, gas, etc.), auxiliary systems (window wipers, controls, pumps, valves, apertures, etc.), positioning systems (laser light, wireless, etc.) and transfer devices (conveyor belt, robotic arms, etc.). For example, the airlock and doors may be opened or closed, all using various electrical signals issued by a computing unit, either directly by the unit or indirectly by an interface that adjusts the signals issued by the computing unit to the voltages, currents, durations, protocols, etc., required to operate the resource.

In various embodiments, the computing unit(s) operate each of the electrically controllable resources in an "open loop" fashion, i.e., without feedback concerning the operation of the resource. For example, the computing unit may operate (i.e., enable, disable, actuate, etc.) each resource according to a pre-programmed schedule without accounting for the effect of the operation.

In various embodiments, the computing unit(s) may also operate a resource in a "closed loop" fashion utilizing an appropriate input (e.g., value, signal, etc.) from a sensor or other monitoring system. For example, the environment of the incubator may be modulated or controlled based upon information provided by one or more sensors. If a computing unit detects via a $CO_2$ sensor that the level of $CO_2$ in an incubator is lower than that required by an executing protocol, then the computing unit may issue a signal to a $CO_2$ source to increase the level of $CO_2$ in the incubator until the sensor indicates that the desired concentration of $CO_2$ has been achieved. The same is true of, e.g., oxygen, humidity, etc., and any other parameter in the incubator that is subject to adjustment utilizing one of the electrically controllable resources.

Figure 3:
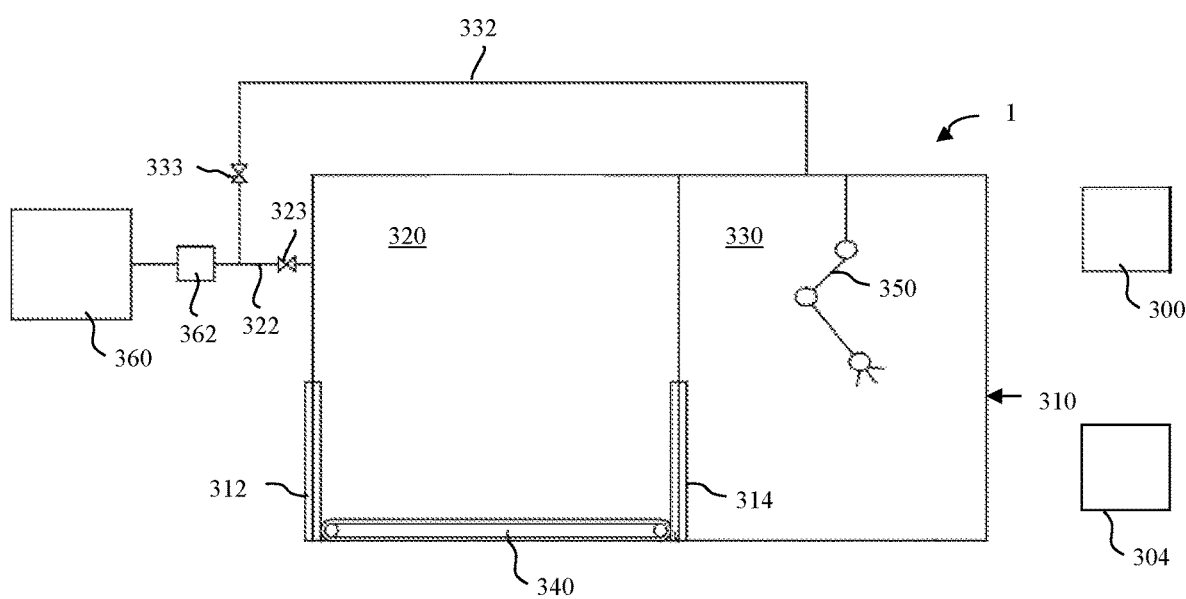
FIG. 3 is a schematic of an illustrative embodiment of a cell culture incubator having a plurality of electrically controllable resources in accordance with one embodiment.

FIG. 3 depicts one illustrative embodiment of a cell culture incubator 1. The cell culture incubator 1 includes an incubator cabinet 310 having internal chambers 320 and 330. An electrically controllable external door 312 opens and closes to permit communication between the internal chamber 320 and the external environment (e.g. the environment external to the incubator cabinet 310). An electrically controllable internal chamber door 314 opens and closes to permit communication between the internal chamber 320 and the internal chamber 330.

The internal chamber 320 and/or the internal chamber 330 may include one or more electrically controllable sensors for determining various internal conditions such as, but not limited to, temperature, humidity, gas content, pressure, and light levels. The internal chamber 320 and/or the internal chamber 330 may include electrically controllable components for adjusting such internal conditions, such as a heater, humidifier, gas generator, air pump, etc.

In some embodiments, an electrically controllable transfer device is positioned within the internal chamber 330. In other embodiments, an electrically controllable transfer device is positioned within the internal chamber 320. In yet other embodiments, the transfer device is positioned in both internal chambers. In other embodiments, the transfer device can freely move between the chambers (such as with a robot that can move between the chambers).

In the illustrative embodiment shown in FIG. 3, an electrically controllable transfer device 350 moves one or more items between the internal chamber 320 and the internal chamber 330. The transfer device 350 may reach into internal chamber 320, pick up one or more items from the internal chamber 320, and move the item(s) into the internal chamber 330. The transfer device 350 may be a robotic arm or any other suitable transfer device described herein.

In some embodiments, more than one transfer device may be included in the cell culture incubator cabinet. In the illustrative embodiment shown in FIG. 3, in addition to the transfer device 350 of the internal chamber 330, an electrically controllable transfer device 340 is included in the internal chamber 320. The transfer device 340 is a belt conveyor system that conveys items from one end of the internal chamber 320 to the other end of the internal chamber 320. As one illustrative example, a computing unit 300 opens external door 312 and places an item on the transfer device 340. The computing unit 300 directs the transfer device 340 to convey the item towards internal chamber door 314, which the computing unit 300 opens to receive the item. The computing unit 300 directs the robotic arm 350 of the internal chamber 330 to move the item off the transfer device 340 and to an appropriate location in the internal chamber 330. Alternatively, the item falls off the conveyor 340 as it approaches the end of the conveyor and lands in internal chamber 330. The computing unit 300 may move the item within the internal chamber 330 by a robotic arm 350 or other transfer device.

In some embodiments, one or more resources in an incubator cabinet and/or on a transfer device may be used by a computing unit 300 to locate and/or align the transfer device. In some embodiments, a location or alignment component may be a physical feature (e.g., one or more protrusions, indentations, guides, etc., or any combination thereof). In some embodiments, a location or alignment component may be electrically controllable by a computing unit 300, such as a signal and/or sensor (e.g., a laser, a camera, an ultrasonic range finder, etc., or any combination thereof).

It should be appreciated that other types of transfer devices may be used as part of the cell culture incubator. For example, in one embodiment (not shown), the cell culture incubator includes a transfer device that includes an electrically controllable linearly actuated receptacle. In this embodiment, the transfer device includes a housing and a receptacle that is translated through the housing using an actuator that is electrically controllable by a computing unit 300. Using the actuator, the computing unit 300 moves the receptacle from one end of the device to the other end of the device. The receptacle can extend at least partially through a first opening at the first end of the transfer device and through a second hole at the second end of the device.

In yet another embodiment (not shown), the internal chamber 320 includes an additional electrically controllable robotic arm type transfer device. It should be appreciated that any number and any type of transfer devices may be included in an incubator (e.g., within one or more chambers of an incubator cabinet).

As described herein, a computing unit 300 may control a sterilization process within internal chamber 320 to sterilize any items added into the internal chamber 320 from the external environment. In one embodiment, a sterilization medium is used as part of the sterilization process. Referring again to FIG. 3, an electrically controllable sterilization medium source 360 is in fluid communication with the internal chamber 320. A pump 362 is used by a computing unit 300 to convey sterilization medium from the sterilization medium source 60 to the internal chamber 320. Alternatively or in addition, the computing unit 300 may use the electrically controllable pump 362 to move sterilization medium from the internal chamber 320 to the sterilization medium source 360. It should be appreciated that pump 362 may be integrated with the source 360 itself. In some embodiments, no pump is included at all.

In one embodiment, the sterilization medium used is ozone. However, it should be appreciated that other types of sterilization medium and corresponding source may be used other than ozone. As such, sterilization medium source 360 may be a source of any suitable sterilization medium.

The computing unit 300 may use the sterilization medium provided to an internal chamber to sterilize the incubator cabinet or other parts of the incubator as part of a cleaning cycle. In one embodiment, during a cleaning cycle, sterilization medium provided by the source 360 is introduced by a computing unit 300 into the internal chamber 320 to sterilize the chamber itself. The computing unit 300 may maintain the internal door 314 in a closed state to prohibit sterilization medium from entering internal chamber 330.

In another embodiment, a computing unit 300 sterilizes both the internal chamber 320 and the internal chamber 330 utilizing various electrically controllable resources. During a cleaning cycle, the computing unit 300 may open the internal door 314 while ozone gas or other sterilization medium is generated or provided from source 360. With the internal door 314 open, sterilization medium may enter into both internal chamber 320 and internal chamber 330.

The computing unit 300 may take any of a number of forms, such as a rack-mounted computer, a desktop computer, a laptop computer, a tablet computer, an embedded computer, a next unit of computing (NUC), etc., integrated into the incubator or external to the incubator and communicating with via a wired or wireless interface (e.g., gigabit Ethernet, 802.11x, etc.). Additionally, the computing unit 300 may be a component not generally regarded as a computer but capable of executing software providing appropriate functionality, such as a Personal Digital Assistant (PDA), a smart phone or any other suitable portable, mobile or fixed electronic device, including the incubator itself.

In various embodiments, the computing unit 300 has one or more input and output devices. These devices can be used, among other things, to present a user interface. Examples of output devices that can be used to provide a user interface include printers or display screens for visual presentation of output, and speakers or other sound generating devices for audible presentation of output. Examples of input devices that can be used for a user interface include keyboards and pointing devices, such as mice, touchpads, and digitizing tablets. In other examples, a computer may receive input information through speech recognition or in another audible format, through visible gestures, through haptic input (e.g., including vibrations, tactile and/or other forces), or any combination thereof.

One or more computing units 300 may be interconnected by one or more networks in any suitable form, including as a local area network (LAN) or a wide area network (WAN) such as an enterprise network or the Internet. Such networks may be based on any suitable technology and may operate according to any suitable protocol and may include wireless networks, wired networks, or fiber optic networks.

With continued reference to FIG. 3, the computing unit 300 may directly route sterilization medium to internal chamber 330. The sterilization medium flow path includes one or more flow controllers 323, 333 (such as valves) that are used by the computing unit 300 to control the sterilization medium flow path. Flow controller 323 controls flow through a internal chamber path 322 and flow controller 333 controls flow through an internal chamber path 332. In one mode, where sterilization medium is desired only in the internal chamber 320, a computing unit 300 closes flow controller 333 while the computing unit 300 opens flow controller 323, and a computing unit 300 keeps the external door 312 and internal door 314 are closed. In another mode, where sterilization medium is desired only in the internal chamber, a computing unit 300 closes flow controller 323, opens flow controller 333, and closes internal door 314. In yet another mode, where sterilization medium is desired in both chambers, a computing unit 300 opens both flow controllers 323, 333 and closes external door 312. The computing unit 300 may open or close internal door 314 in this mode.

As depicted in FIG. 3, the computing unit 300 may be used to control one or more components of the cell culture incubator 1. For example, the computing unit 300 may control the sterilization medium source 360, pump 362 and/or 364, external door 312, internal door 314, transfer device 340, 350 and/or 370, sensors, and any components that affect the internal conditions of the incubator (e.g., heaters, humidifiers, gas generators, etc.). The computing unit 300 may be external to the incubator cabinet, as seen in FIG. 3. The computing unit 300 may receive information from one or more sensors located inside the incubator cabinet 310 (sensors may be in the internal chamber 320 and/or the internal chamber 330). The computing unit 300 may communicate with one or more components of the cell culture incubator 1 and/or the sensors via wireless signals and/or wired signals.

As described herein, the computing unit 300 uses the electrically controllable resources of the incubator to provide and maintain appropriate temperature, and gas mixtures for cell growth. It should be appreciated that cell growth conditions differ for different cell types and that the incubators described herein can be programmed to maintain different conditions that are appropriate for each cell type.

In some embodiments, the computing unit 300 and the electrically controllable resources described herein monitor or assay culture media for nutrient depletion, changes in pH, changes in temperature, accumulation of apoptotic or necrotic cells, and/or cell density. In some embodiments, the computing unit 300 and the electrically controllable resources described herein are used to modify or change the culture media or conditions and/or to passage the cell cultures when appropriate. In some embodiments, these procedures are automated.

In some embodiments (e.g., for adherent cell cultures), the computing unit 300 can use electrically controllable resources to directly remove or aspirate culture media and/or replace it with fresh media. In some embodiments (e.g., for non-adherent/suspension cultures), media changes can involve centrifuging a cell culture, removing the old culture media and replacing it with fresh media. In some embodiments, the centrifuge is an electrically controllable resource located in the internal chamber of an incubator subject to operation by a computing unit. In some embodiments, culture vessels allow for continuous media replacement.

In some embodiments, the incubators 1 described herein may include one or more electrically controllable components that can be used to process, replace, supply, and/or maintain different aspects of a culture media to support cells, such as electrically controlled reservoirs containing waste media and/or fresh media. Such reservoirs may be present (e.g., for temporary storage) within an electrically controlled refrigerator inside the incubator or a refrigerated section thereof.

In some embodiments, one or more reservoirs are provided outside the incubators and electrically controlled plumbing is provided into and out from the incubator space to supply or draw from a liquid handler unit (e.g., liquid handle units having an aspirator) or temporary reservoir within the incubator to facilitate cell feeding, media changes, and other related needs. For suspension cells, electrically controlled devices may be provided within the incubator to separate cells from waste media (e.g., computing unit controlled centrifuge(s) to facilitate cell pelleting) to facilitate automated media changes as part of an incubator provided herein.

One or more incubators 1 in various embodiments may be configured with transportation technology to transport certain items. Not only may plates and other equipment be moved within an incubator (e.g., via transfer devices 340 and 350), but plates and other equipment may be transported between two or more incubators 1 as well as between other types of devices, systems, instruments, laboratory equipment, or the like (e.g., assay machines, spin column kits, sequencing systems, cell isolation platforms, cell tissue storage devices, etc.). These plates and other equipment may be transported between these devices via, for example, bridges, ports, or other connections that enable movement of the plates or other items outside of an incubator or other type of device.

In certain embodiments these may be sealed connection mechanisms. That way, samples are not contaminated as they are being transferred from one device to another. In other embodiments, the connection mechanism may not be sealed.

In some embodiments, the connection mechanism may be configured as a conveyor belt such as the transfer device 340. In these embodiments, the conveyor belt(s) may extend from a first incubator to a second incubator. These types of conveyor belts may be configured as an enclosed bridge that can move (i.e., shuttle) plates or other types of equipment to other incubators or other types of systems or instruments.

The shuttle devices of various embodiments may be controlled by a computing unit 300 as required by the various scheduler modules described herein. Accordingly, these shuttle devices may link various types of systems that vary in complexity and purpose.

The shuttle devices enable the dynamic allocation of resources and therefore increase the number of options for scheduling various tasks. Accordingly, the scheduling modules may consider the functions and availability of a plurality of incubators, including their ability to transfer samples therebetween, when generating schedules in accordance with various embodiments described herein.

Incubators 1 of various embodiments may also be configured to receive one or more consumable transporters. These transporters may be configured as container devices with a plurality of receptacles to store or otherwise house certain types of consumables, equipment, tools, samples, plates, or the like.

These consumable transporters may be readily moved from one incubator to another incubator (e.g., by an operator). Accordingly, operators such as lab personnel or the like may have ready access to various consumables within the incubator 1. Additionally, the contents of various receptacles may be known by the computing unit 300. Accordingly, in operation, the robotic arm as illustrated in FIG. 3 may be instructed to reach for a particular receptacle to access a particular consumable, sample, plate, tool, or the like.

These transporters may also be configured with identification tags. For example, the transporters may include a barcode label, a QR code label, an RFID tag, or another type of identification label. These labels allow systems and operators to track the contents of the transporter. Each system may be configured with a scanning device to scan the label to determine the contents of the incoming or outgoing transporter.

The transporter of various embodiments may also be suited to sterilization by, e.g., autoclave (e.g., through pressure and heat). Accordingly, in some embodiments, a transporter may be loaded, sterilized, and then placed into an incubator.

Figure 4:
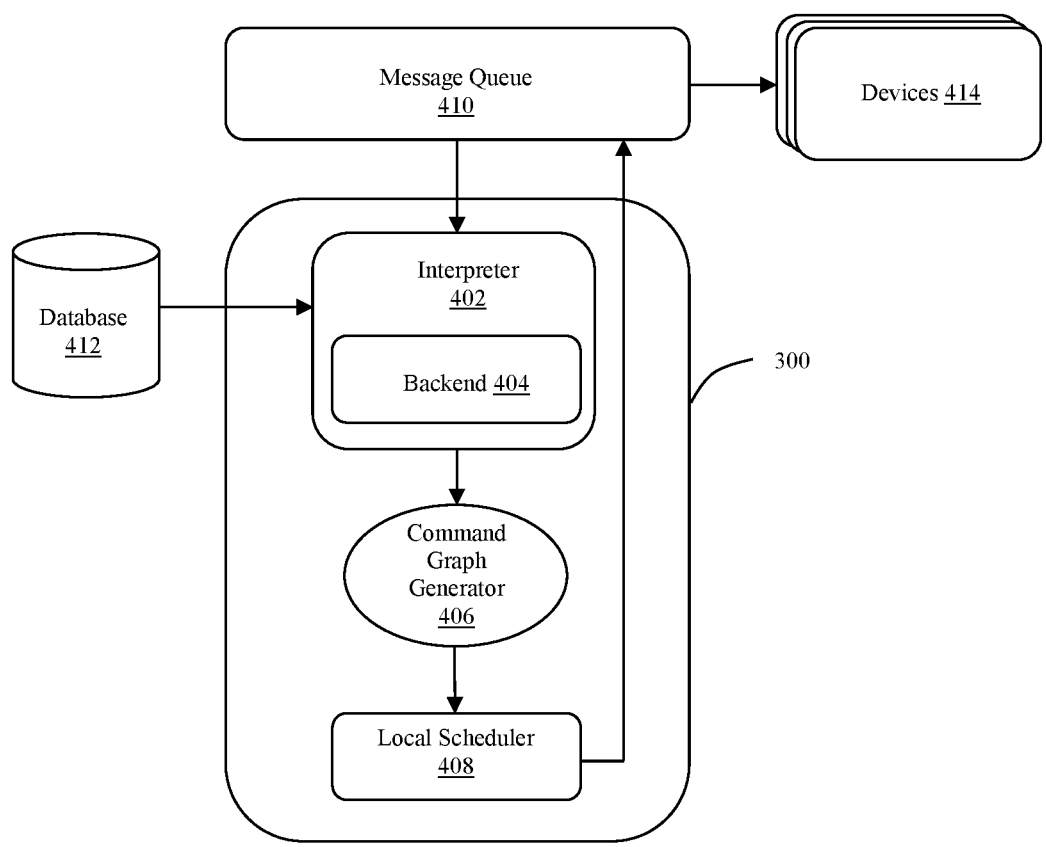
FIG. 4 illustrates the computing unit of FIG. 1 in accordance with one embodiment.

FIG. 4 illustrates the computing unit 300 of FIG. 3 in accordance with one embodiment. There may be a computing unit 300 configured with or otherwise in operable communication with each incubator.

The computing unit 300 may include an interpreter module 402 with a backend component 404, a command graph generator 406, and a local scheduler module 408.

The computing unit 300 may be in operable communication with a message queue 410 that at least receives data regarding one or more protocol runs to be executed. Data regarding the protocol runs may be communicated via the advanced messaging queueing protocol (AMQP), for example. The message queue 410 may then pass data regarding one or more protocol runs to the interpreter module 402. The computing unit 300 may also learn from previous protocol runs. For example, a database 412 may store data regarding statistical distributions of durations, and the computing unit 300 can learn from this data as well as from user reinforcement and feedback. This information may include durations of particular tasks, for example.

In addition to receiving data regarding protocol runs from the message queue 410, the interpreter module 402 may also be in communication with and receive machine state data from the database 412. The interpreter module 402 may be configured to merge data regarding protocol runs, operational settings, cell line specific settings, and machine state into an executable protocol. Additionally, the interpreter module 402 may interpret procedures of a particular protocol into one or more appropriate commands.

In the context of the present application, the terms "machine state" may refer to characteristics of one or more devices at a given time. Exemplary values for "machine state" may include, but are not limited to, reagent plate and well locations, cell plate location(s) and well locations, tip rack and next index, or the like. Exemplary cell line specific settings may include, but are not limited to, exposure time, gain, and maximum disassociation duration.

The backend module 404 may be a specially configured processor or the like that knows how to execute each procedure step on a specific system. The backend module 404 may know where to move a certain pipettor device to eject a tip, how far to move a certain component, how quickly to move a certain component, how often to capture imagery, etc.

For example, a given protocol may include the steps:
(1) Transfer Liquid {1 mL, from Media Well 3, to Source Well 1};
(2) Focus {20×}; and
(3) Acquire {20×, for 120 seconds every 15 seconds}.

The interpreter module 402 (and the backend module 404) may interpret these steps and translate them into actionable commands to be executed by the various devices 414. For example, the backend module 402 may output a command list include steps (1) MoveTo Pipettor TipStation Index-1; (2) GetTip Pipettor; (3) MoveTo Pipettor MediaStation Well-3; (4) Aspirate Pipettor 1.0; (5) MoveTo Pipettor Mainstation Well-1; (6) Dispense Pipettor 1.0; (7) MoveTo Pipettor DisposalStation; (8) EjectTip Pipettor; (9) MoveTo 20× Mainstation Well-1; (10) Focus 20×; and (11) Acquire 20× 120 15.

In other words, a protocol may involve transferring a liquid from a first location to a second location, and then gathering imagery of the liquid. To accomplish this, the interpreter module 402 breaks these steps into a series of commands that are executable by one or more devices 412 of the incubator 1. The eleven commands listed above may specify, for example, which pipettor tip (index) needs to be picked up, which well is holding the liquid of interest, the level of focus for an image gathering device, and how often images are to be captured (as well as how many images are to be captured).

Figure 5:
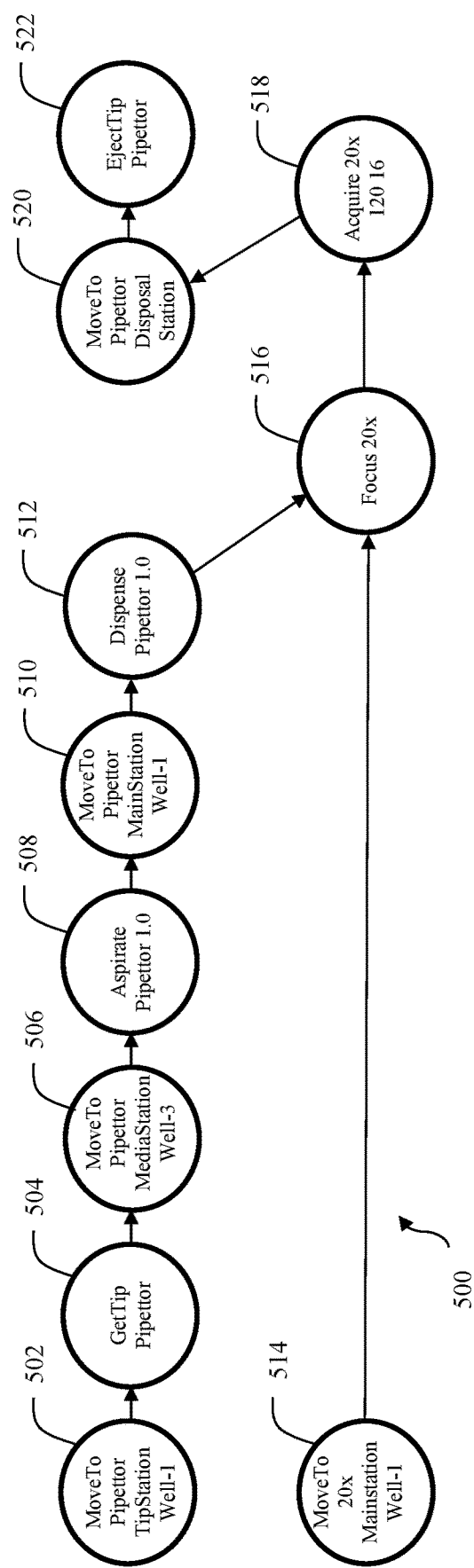
FIG. 5 illustrates a command graph in accordance with one embodiment.

The command graph generator 406 may output or otherwise present the commands in the form of a command graph such as the command graph 500 of FIG. 5. The command graph 500 may comprise the several commands listed above. The arrows connecting each command may indicate that the commands connected therewith are consecutive commands. That is, the arrows may imply that a particular command is required to be executed before another command, thereby implying a level of temporal dependence. For example, and with reference to command graph 500 of FIG. 5, the command 504 "GetTip Pipettor" must execute before command 506 "MoveTo Pipettor MediaStation Well-3," which must execute before 508 "Aspirate pipettor 1.0." This is of course logical as a pipettor device must be gathered before it can be moved.

With continued reference to command graph 500 of FIG. 5, the command 514 "MoveTo 20× MainStation Well-1" is only required to be executed before the command 516 "Focus 20×." Command 514, however, is independent from the commands 502-512 and may occur before, during, or after any of the commands 502-512 as long as it is executed before command 516.

Figure 6:
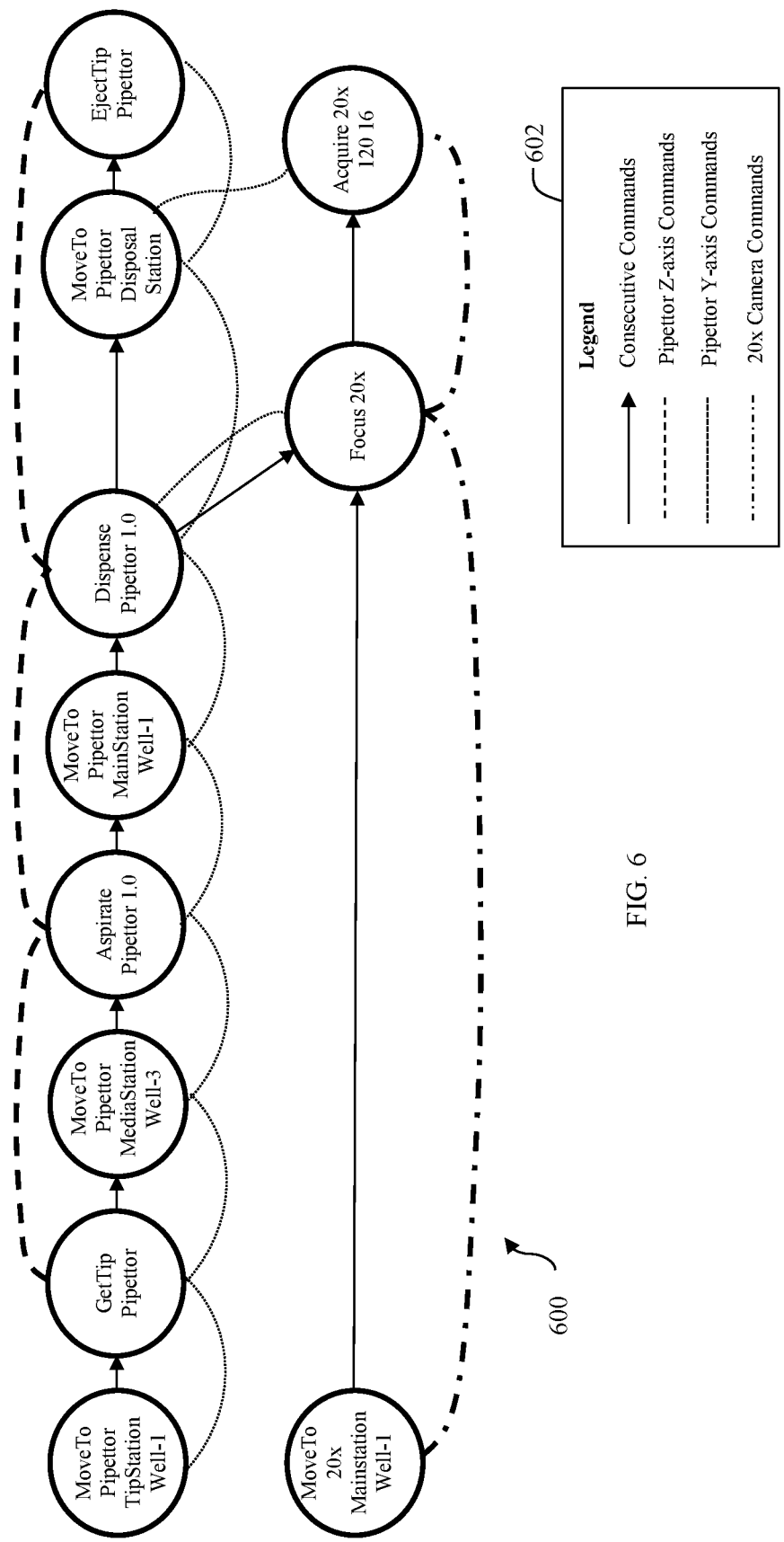
FIG. 6 illustrates a resource-command graph in accordance with one embodiment.

FIG. 6 illustrates a resource-command graph 600. The commands shown in the graph 600 are the same as the commands shown in the command graph 500 of FIG. 5. In addition to showing these commands, the resource-command graph 600 also shows the resources used to perform each command step. More specifically, the resource-command graph 600 highlights commands that share (are performed) by the same electrically controllable resource. These resources are listed and identified in legend 602. For example, command "Aspirate Pipettor 1.0" and the command "Dispense Pipettor 1.0" use the same resource.

In operation, and as discussed above, commands can be executed at any time if they have no incoming edges. As can be determined from studying the resource-command graph 600, only one command per resource can execute at a time. Further, commands are removed from the graph when they complete.

Figure 7:
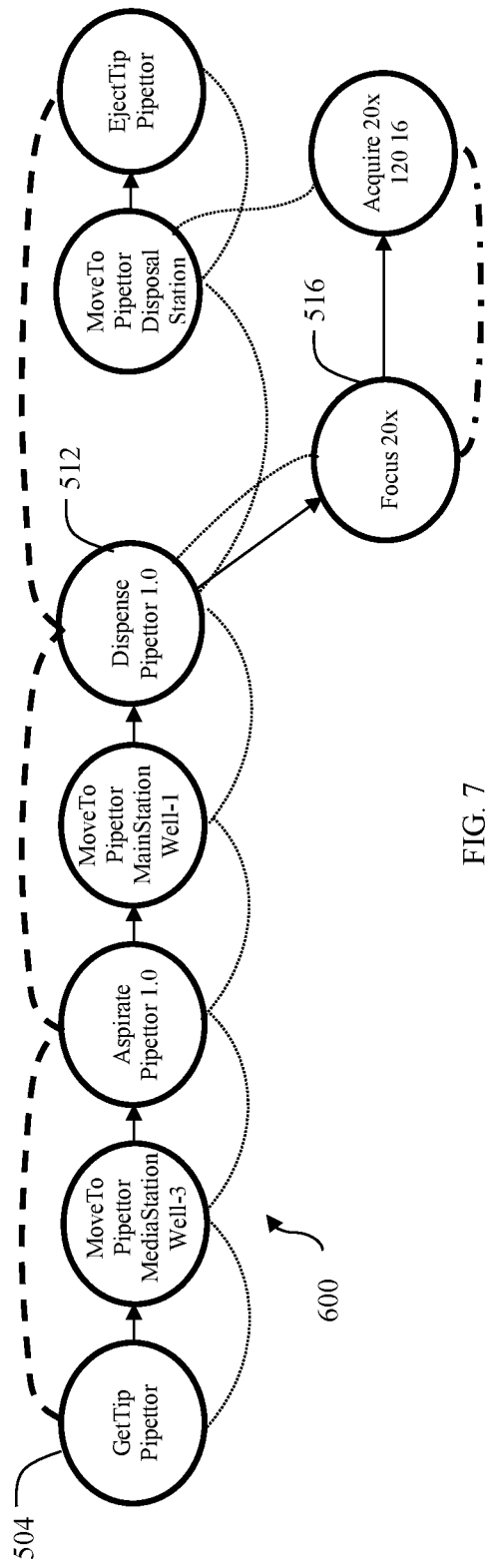
FIGS. 7-9 illustrate the resource-command graph of FIG. 6 during command execution in accordance with one embodiment.

For example, FIG. 7 illustrates the resource-command graph 600 of FIG. 6, with two commands removed because they have been executed. Specifically, command "MoveTo Pipettor TipStation Well-1" and command "MoveTo 20× Mainstation Well-1" have been executed and have been removed from the graph. In accordance with the rules that commands can be executed if they have no incoming edges, the command "GetTip Pipettor" (step 504 in FIG. 5) can now be executed since there are no other previously required steps. Although the command "MoveTo 20× ManStation Well-1" (step 514 in FIG. 5) has been executed and removed, command "Focus 20×" (step 516 in FIG. 5) cannot be executed yet because the command "Dispense Pipettor 1.0" (step 512) still must be executed.

Figure 8:
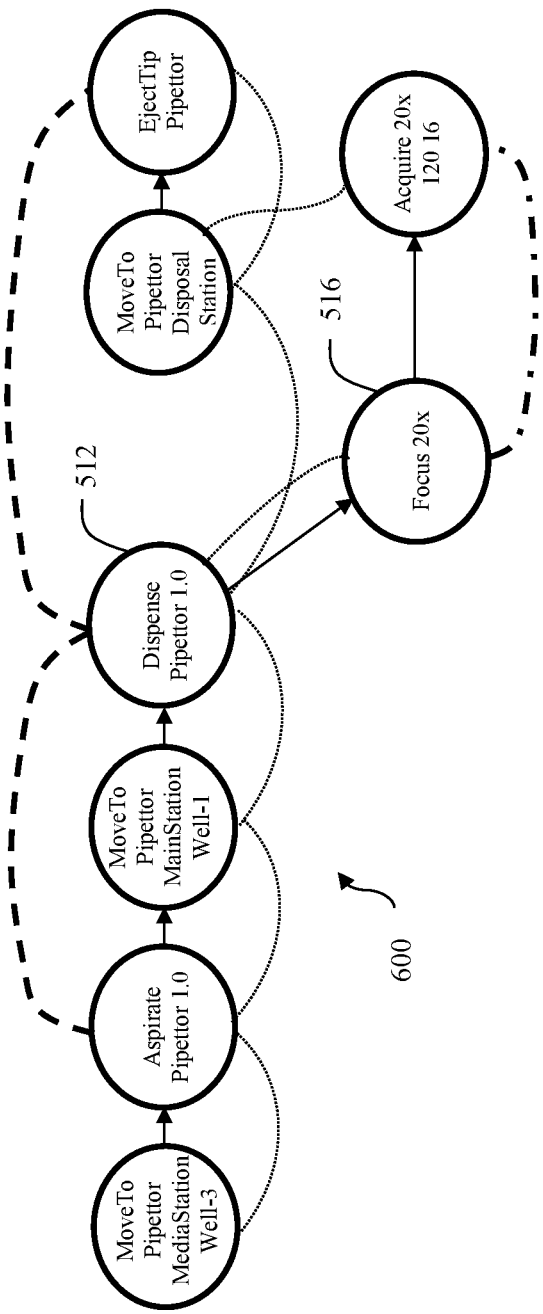

FIG. 8 illustrates the resource-command graph 600 of FIG. 6, with another command (step 504) removed. Command "GetTip Pipetter" has been executed, and therefore command "MoveTo Pipettor MediaSation Well-3" can now be executed.

Figure 9:
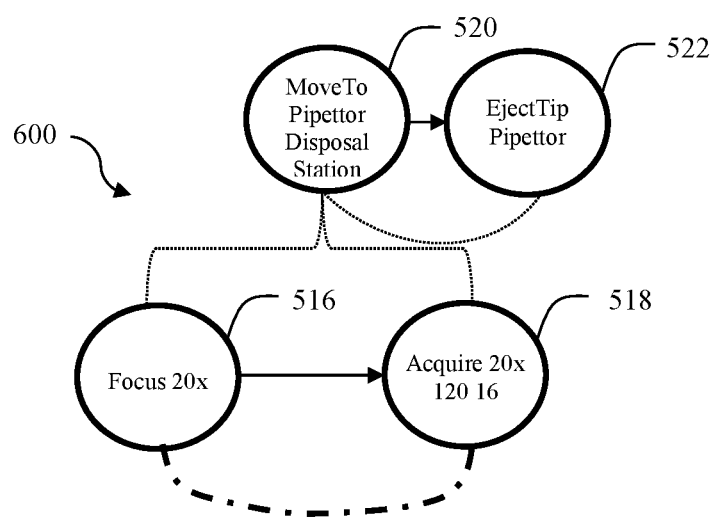

Subsequent commands may be executed accordingly. FIG. 9 illustrates the resource-command graph 600 after several commands have been executed and only steps 516, 518, 520, and 522 are remaining. At this point, the local scheduler module 408 may either execute command "MoveTo Pipettor Disposal Station" (step 320) or execute command "Focus 20×"(step 316). It is noted that these commands cannot be performed simultaneously as they both share the same resource.

In this particular instance, the local scheduler module 408 may decide which step to execute in a variety of ways. In some embodiments, the local scheduler module 408 may consider one or more heuristics to determine the order in which to execute two or more commands. In the context of the present application, the term "heuristics" may refer to rules that are generally quick and easy to implement.

For example, the local scheduler module 408 may be configured to execute commands in order based on their descending levels of priority. That is, the local scheduler module 408 may first execute the command with the highest priority. The local scheduler module 408 may then execute the command with the second highest priority and so on. Priorities may vary and may depend on the particular sample being analyzed, the configuration of the incubator, preferences of a particular cell culturist, or the like. For example, the command "EjectTip Pipetter" may, in some embodiments, always be a high priority to prevent residual fluid from dripping from the pipette.

Another heuristic may be based on the (expected) duration of a command. For example, the local scheduler module 408 may be configured to first execute the command with the shortest temporal duration, and then execute the command with the second shortest temporal duration, and so on. As another example, the local scheduler module 206 may be configured to first execute the command with the longest temporal duration, and then execute the command with the second longest temporal duration.

Data regarding the temporal durations of particular commands may be derived from previous command executions. The database 412 may be configured to store data regarding how much time particular commands generally require to execute. This data may be continuously updated with each execution, and the local scheduler module 408 may consider the average duration of all executions of a particular command, a moving average of executions of a particular command, an exponential moving average of a particular command, or the like. The expected duration can also be based on knowledge and settings of a particular incubator and/or incubator device, such as how fast a particular motor generally operates. Similarly, an operator or the like may input data regarding an expected temporal duration of a particular command.

In accordance with a variation of heuristics, the local scheduler module 206 may execute particular commands based on improvements in heuristic-based executions. That is, the local scheduler module 408 may start with a sub-optimal solution, and then search to improve on the sub-optimal solution. These solutions may be based on techniques such as genetic algorithms, simulated annealing, and other optimization techniques known in the art.

The local scheduler module 408 may also use scheduling techniques referred to as approximate solutions. These techniques are those that are guaranteed to be within a fixed percentage of the optimal solution. However, these solutions are generally slower to compute.

Various embodiments of the present invention may also utilize various other optimization algorithms such as "branch and bound" based techniques, Monte Carlo simulation techniques, and linear programming techniques to achieve optimal schedules. These may also include non-stochastic simulations such as real-time simulations or accelerated-time simulations.

The local scheduler module 408 may also search for and determine the best schedule by optimizing for certain criteria. This criteria may include cell health (e.g., to achieve the best cell health), least cell stress, fastest cell growth, maximum plate throughput, minimum consumable/reagent usage, minimum power consumption, or the like.

The local scheduler module 408 may also optimize reagent loading. That is, the local scheduler module 408 may optimize the reagent loading procedure to maximize walk-away time and/or most efficiently use the limited storage for a particular reagent.

Figure 10:
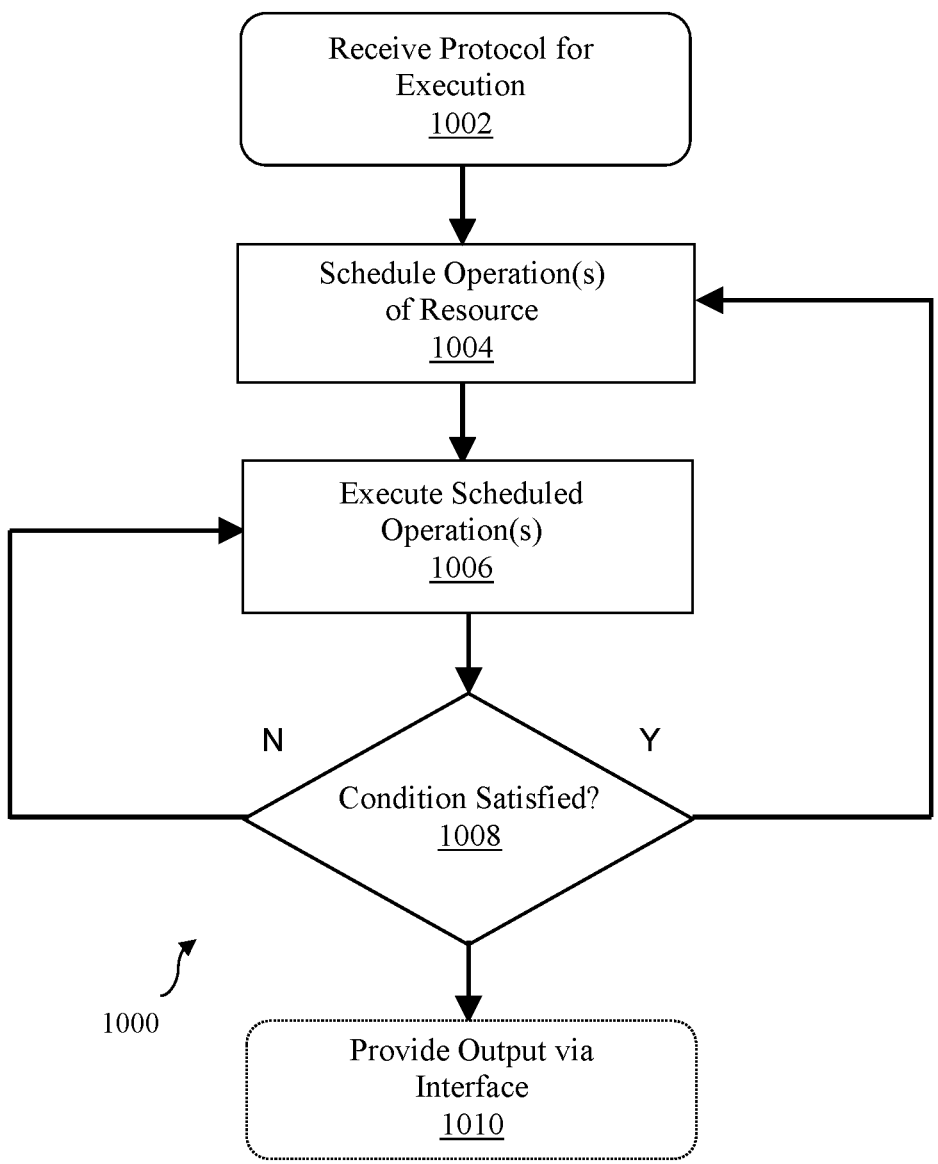
FIG. 10 depicts a flowchart of an exemplary method for operating a cell culture incubator having a plurality of electrically controllable resources in an autonomous mode in accordance with one embodiment.

FIG. 10 depicts a flowchart describing an exemplary embodiment of a method 1000 for operating an incubator in autonomous mode. In this embodiment, a computing unit receives a predefined protocol describing how the computing unit is to operate one or more electrically controllable resources of the incubator (Step 1002). The protocol may be manually specified by an operator using a user input or it may be retrieved from a non-transient storage medium that may be local to the incubator or accessed by the computing unit using, e.g., a wired or wireless network connection.

Having received the protocol, the computing unit parses the steps specified by the protocol and proceeds to schedule the operation of at least one of the incubator's electrically controllable resources (Step 1004). Once at least one of the resources has been scheduled, the computing unit can proceed to execute the scheduled operations of the electrically controllable resources and thereby perform the protocol (Step 1006).

As the operations are executed, the computing unit executes various computer-readable instructions that check to see if various conditions are satisfied while the protocol is executing (Step 1008). If a condition is met, it may result in a change in the execution of the protocol, such as the rescheduling of the operation of at least one electrically controllable resource (Step 1004). For example, one such protocol may involve scheduling an imaging operation of a cell culture every four hours to determine whether it is time to move the culture to a different chamber.

If no condition is satisfied, the computing unit will continue to execute the operations (Step 1006) of the electrically controllable resources that it had previously scheduled (Step 1004). When the protocol is completed, various results may be provided to an operator via a user interface (Step 1016).

As discussed above, the conditions may constitute a conditional test that is satisfied when a value meets a certain specified value or falls within a certain specified range. Example conditions may be, e.g., a certain cell type, the occurrence of a certain action such as the receipt of a user input, a material shortage, a certain sensor input, etc.

In some embodiments, the scheduling operation (Step 1004) may involve the computing unit simulating the operation of the protocol utilizing, e.g., scheduling algorithms (Monte Carlo scheduling) or heuristics to identify the optimal order for scheduling the incubator resources. The initial scheduling or rescheduling of the resources may be varied by the computing unit to account for the results of the simulation.

The scheduling algorithms, in some cases, may be considered distinct from simulation algorithms like Monte Carlo, simulated execution, etc. Heuristics may be used both for simulation (e.g., to decide how long a step is likely to take) or for scheduling. In one embodiment, in general, the simulation step provides one or more possible execution scenarios for a protocol (e.g., time ranges, resources required, etc.) which are then considered by a planning/scheduling algorithm. Note that a reschedule due to changes in observed conditions or improved simulations might be a distinct process from the initial scheduling procedure.

Simulating execution of a protocol prior to scheduling and/or executing the protocol offers several advantages. For example, simulation may allow a computing unit to determine in advance, the amount of consumables needed to execute the protocol as well as the timing for using those consumables.

As protocols become more complicated and event driven (e.g., with events triggered upon the satisfaction of a precondition as opposed to events being triggered at a particular time), it becomes difficult to accurately predict the execution of a protocol, including the timing and use of various consumables. Various embodiments use a variety of techniques to improve the accuracy of these predictions as protocols become complex.

In some embodiments, simulation of the protocol accounts for the kinematics and dynamics of various electrically controllable incubator resources. In some embodiments, protocols with actions conditioned on the completion of various prerequisite conditions (e.g., steps, actions, etc.) are simulated using various assumptions about the timing of the completion of these preconditions. In these embodiments, the result of the simulation will typically be a range of expected values and confidence levels for the simulation as opposed to an exact result. The results of the simulation process may be presented to users in a variety of forms, including but not limited to a graphical display, a timeline, etc.

In some embodiments the assumptions used in simulation may be preloaded into a nonvolatile storage, specified by an operator, or both. In some embodiments the assumptions or the simulation itself may utilize the results of past protocol runs or past simulations. In some embodiments, protocol simulation may involve multiple simulations or alternate simulations to confirm the results of a simulation or develop a range of expected values for particular elements in the simulation.

In some embodiments an operator may edit the results of the simulation. In some embodiments the simulation process is performed once before the protocol is run. In some embodiments the simulation process runs in tandem with the execution of the protocol, and the partial results of execution are used as inputs to the simulation process; results from the revised simulation may be presented to an operator, which may in turn result in additional operator or incubator actions in connection with execution of the protocol (e.g., rescheduling operations, rescheduling consumable replenishment, etc.).

While embodiments of the invention may operate in a fully autonomous mode, i.e., under the control of a computing unit executing a protocol, various embodiments may also operate in interactive or semi-autonomous modes, allowing users to interact with the incubator as it executes a protocol and thereby influence or control the execution.

Figure 11:
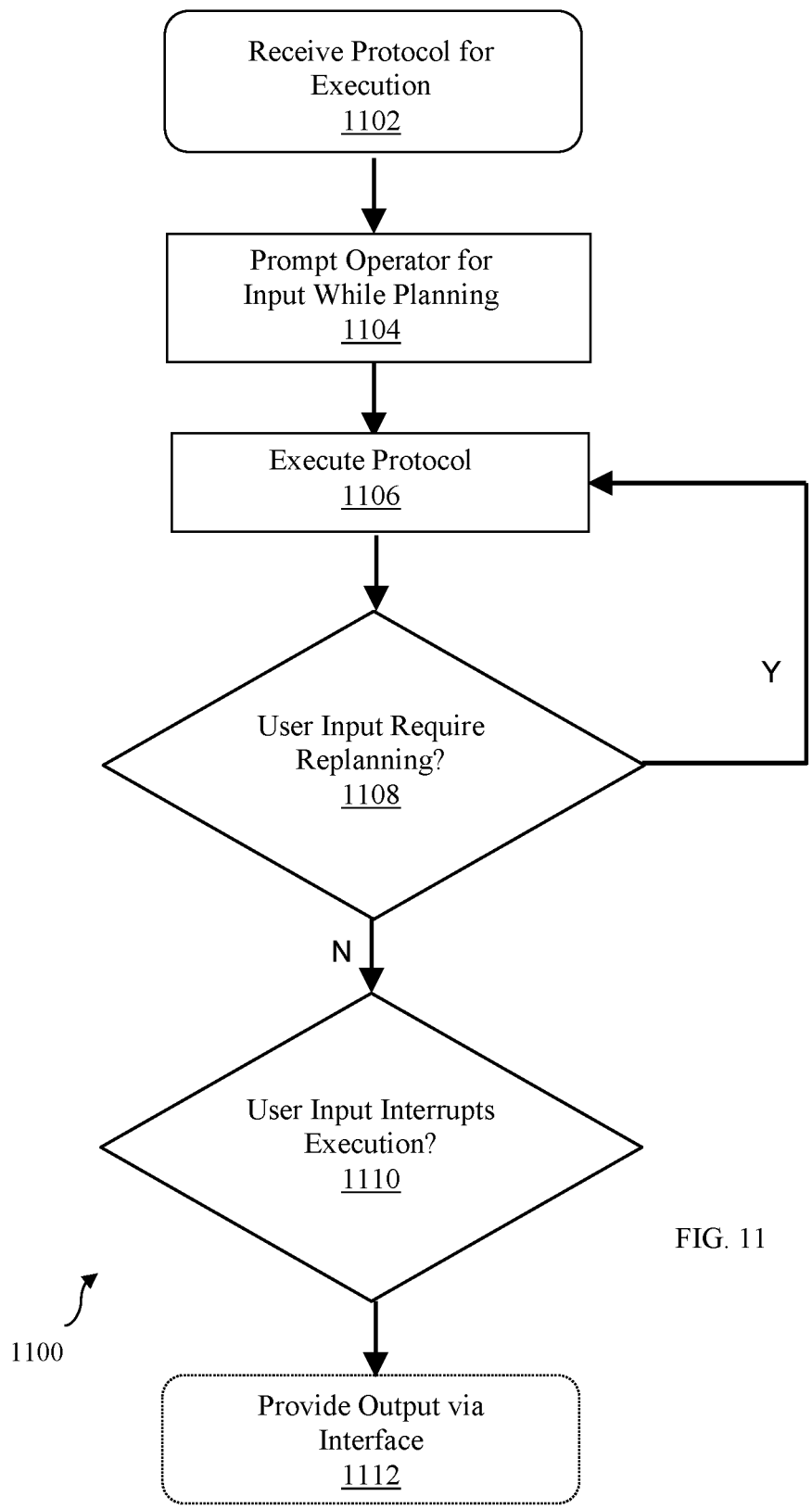
FIG. 11 depicts a flowchart of an exemplary method for operating a cell culture incubator having a plurality of electrically controllable resources in an interactive mode in accordance with one embodiment.

FIG. 11 presents a flowchart describing an exemplary embodiment of a method 1100 for operating an incubator in an interactive mode. In this embodiment, a computing unit receives a predefined protocol describing how the computing unit is to operate one or more electrically controllable resources of the incubator (Step 1102). The protocol may be manually specified by an operator using a user input or it may be retrieved from a non-transient storage medium that may be local to the incubator or accessed by the computing unit using, e.g., a wired or wireless network connection.

As discussed above in connection with FIG. 11, various prerequisite operations (scheduling, etc.) may be performed in preparation for protocol execution. The incubator may prompt the operator for input (Step 1104) as it prepares to execute the protocol. For example, the operator may be prompted to confirm a scheduled protocol before it executes, the operator may be prompted to replenish incubator supplies or reconfigure the arrangement samples in the incubator and to confirm these actions before executing the protocol, etc. If the operator fails to provide the solicited information or take the solicited action within a predetermined time period, then the incubator may substitute default options or choices determined using heuristics during the planning process.

Once the planning process is completed, the incubator executes the protocol (Step 1106). The incubator may, e.g., poll various input peripherals connected to the incubator for user input or it may operate on an interrupt-driven basis, responding when a user provides an input to the incubator. At various points during protocol execution, a user may be prompted for input and/or a user may enter an input requiring attention from the incubator. For example, at some point during protocol execution the incubator may collect information that requires user attention, confirmation, or some other kind of decision. Continuing this example, the system itself may present a recommendation that the user can accept or reject, or that the system may automatically deem accepted or rejected if the user does not supply an input within a certain period of time. The information and an appropriate prompt may be presented to an operator using a user interface.

In some cases, the input supplied by the user may be merely confirmatory or otherwise consistent with the execution of the protocol. In other cases, the user input may require rescheduling the remaining operations for the protocol, either through the introduction of a simple delay or utilizing simulation to determine a revised execution schedule for the remaining operations. In some embodiments, the incubator will receive the proposed interruption and, before interrupting execution, execute a simulation accounting for the interruption, advise the operator of the consequences of interrupting execution (e.g., the violation of important timing constraints), and seek confirmation of the proposed interruption before permitting the interruption of the execution. The incubator evaluates the received input (Step 1108) and, if necessary, reschedules the protocol and starts or continues the execution of the scheduled protocol (Step 1106).

In some cases, the user input may interrupt a protocol that is executing as scheduled to permit the operator to request certain actions be performed immediately (Step 1110). For example, an investigator may request the imaging of a particular well or wells. By way of contrast, these types of operations do not require the interruption or rescheduling of protocol execution. When the protocol is complete, output may be provided to one or more users via an appropriate interface (Step 1112).

In some embodiments, the operator may enable or disable the semi-autonomous mode during the execution of the protocol, putting the incubator in the aforementioned autonomous mode.

Figure 12:
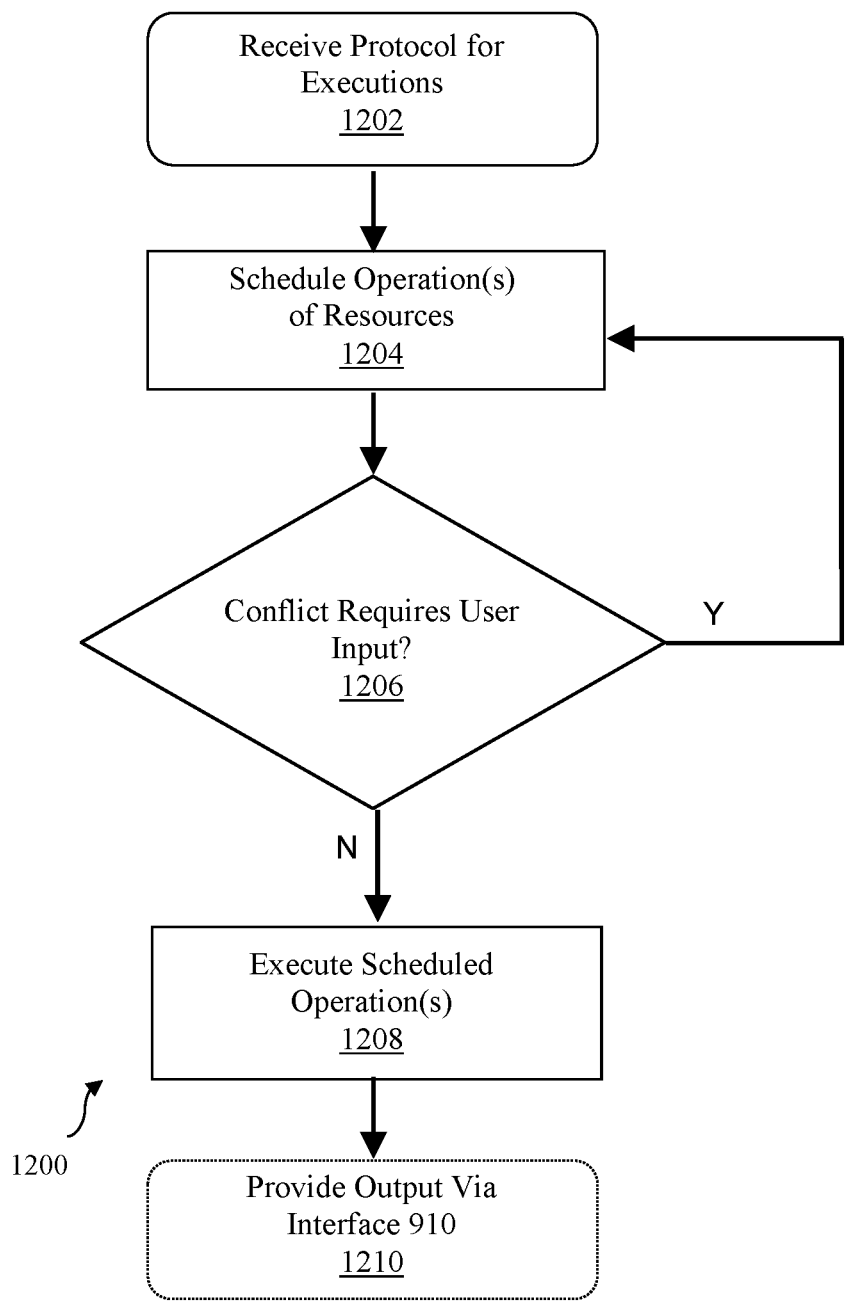
FIG. 12 depicts a flowchart of an exemplary method for programming a cell culture incubator with a plurality of simultaneously executing protocols in accordance with one embodiment.

In some incubators, multiple protocols may be executed simultaneously. With reference to FIG. 12, in these embodiments, while otherwise similar to the process for planning and executing a single protocol as described in FIG. 10 and the associated text, the aforementioned simulation and scheduling operations (Step 1204) may consider the plurality of protocols to be executed in these incubators. In particular, the scheduling and simulation operations may consider that, e.g., while multiple protocols may execute concurrently, they may still have different start and stop times and that those times may be selected by the computing unit utilizing the results of protocol simulation. In some embodiments the simulation of multiple concurrent protocols may identify that a proposed combination of protocols is incompatible (i.e., they are impossible to execute concurrently due to conflicts over use of internal modules, transport resources, inadequate internal storage for consumables, etc.) and alert the operator as to the incompatibility and offer a variety of user selected options to resolve the conflict (Step 1206). The scheduled operations may be executed once any conflicts are resolved (Step 1208). When the protocol is complete, output may be provided to one or more users via an appropriate interface (Step 1210).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to.

Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A cell culture incubator instrument comprising:
   an incubator cabinet having internal chambers, a door for providing communication between the internal chambers and an external environment and an electrically controllable door between the internal chambers;
   a plurality of electrically controllable resources including an electrically controllable device for handling a liquid medium in at least one of the internal chambers, an electrically controllable transfer device for moving one or more items in and out of the internal chambers, and electrically controllable cell culture vessel transfer device for moving at least one cell culture vessel within one internal chamber;
   a processor; and
   a non-transitory computer-readable medium having instructions stored thereon that define at least one protocol and that, when executed by the processor, enable the processor to:
      receive data regarding at least one protocol to be performed by the instrument;
      generate a schedule regarding operation of at least one of the plurality of electrically controllable resources to perform the at least one protocol; and
      control at least one of the plurality of electrically controllable resources in accordance with the generated schedule of the plurality of electrically controllable resources, wherein:
         at least one prerequisite operation is performed in preparation for a protocol execution;
         the prerequisite operation prompts a user fora first input; and
         the processor is configured to substitute a second input using heuristics upon the failure of the user to provide the first input within a predetermined time period.

2. The instrument of claim 1, wherein the plurality of electrically controllable resources include resources in the incubator cabinet and/or on the transfer device used by the processor to locate and/or align the transfer device.

3. The instrument of claim 1, wherein the instructions include at least one conditional action that specifies activation of at least one electrically controllable resource in response to a satisfied condition.

4. The instrument of claim 1, wherein the instructions include at least one range-bound conditional action specifying the activation of at least one electrically controllable resource in response to a condition falling within a predetermined range.

5. The instrument of claim 1, wherein the instructions include at least one self-modifying conditional action changing at least one of the actions specified by the conditional action or the condition of the conditional action in response to data received by the processor.

6. The instrument of claim 3, wherein the condition comprises at least one of a cell type and an action performed by the at least one electrically controllable resource.

7. The instrument of claim 1, wherein the processor learns by using data from at least one previous protocol run to modify a future protocol run.

8. The instrument of claim 1 wherein the instructions provide for rescheduling a previously scheduled operation of at least one of said plurality of electrically controllable resources.

9. The instrument of claim 8, wherein the instructions provide for rescheduling a previously scheduled operation in response to at least one of a material shortage and a user action.

10. A cell culture incubator instrument comprising:
    an incubator cabinet having internal chambers, a door for providing communication between the internal chambers and an external environment and an electrically controllable door between the internal chambers;
    a plurality of electrically controllable resources including an electrically controllable device for handling a liquid medium in at least one of the internal chambers, an electrically controllable transfer device for moving one or more items in and out of the internal chambers, and electrically controllable cell culture vessel transfer device for moving at least one cell culture vessel within one internal chamber;
    a processor; and
    a non-transitory computer-readable medium having instructions stored thereon that define at least one protocol and that, when executed by the processor, enable the processor to:
       receive data regarding at least one protocol to be performed by the instrument;
       generate a schedule regarding operation of at least one of the plurality of electrically controllable resources to perform the at least one protocol; and
    control at least one of the plurality of electrically controllable resources in accordance with the generated schedule of the plurality of electrically controllable resources, wherein during a protocol execution a user is prompted for an input and wherein the processor is configured to substitute an input using heuristics upon the failure of the user to provide an input within a predetermined time period.

11. The instrument of claim 3, further comprising at least one user input device, and wherein the instructions provide for receiving an input from said at least one user input device.

12. The instrument of claim 1, wherein the processor is in communication with and receives machine state data from a database to merge data regarding protocol runs, operational settings, cell line specific settings, and machine state into an executable protocol.

13. The instrument of claim 1, wherein the instructions provide for simulating the scheduled operation of at least one of said plurality of electrically controllable resources.

14. The instrument of claim 13, wherein the instructions for scheduling operation utilize the results of the simulation to schedule the operation of at least one of said plurality of electrically controllable resources.

15. The instrument of claim 13, wherein the simulation of the scheduled operation utilizes at least one of Monte Carlo simulations and non-stochastic simulations.

16. The instrument of claim 1 wherein the instructions for scheduling operation utilize at least one of scheduling algorithms and scheduling heuristics selected from the group consisting of task priority heuristics, task duration heuristics, improvement heuristics, and approximate solution-based heuristics.

17. A networked cell culture incubator instrument system, the system comprising:

a database;

a plurality of cell culture incubator instruments in operable communication with the database, wherein each of the plurality of instruments includes:

an incubator cabinet having internal chambers, a door for providing communication between the internal chambers and an external environment and an electrically controllable door between the internal chambers;

a plurality of electrically controllable resources including an electrically controllable device for handling a liquid medium in at least one of the internal chambers, an electrically controllable transfer device for moving one or more items in and out of the internal chambers, and electrically controllable cell culture vessel transfer device for moving at least one cell culture vessel within one internal chamber;

a processor; and a non-transitory computer-readable medium having instructions stored thereon that define at least one protocol and that when executed by the processor, enable the processor to:

receive data regarding at least one protocol to be performed by the instrument, generate a schedule regarding operation of at least one of the plurality of electrically controllable resources to perform the at least one protocol, control at least one of the plurality of electrically controllable resources in accordance with the generated schedule of the plurality of electrically controllable resources; and a global scheduling device in operable communication with the database and including a processor and a non-transitory computer-readable medium having instructions thereon that when executed by the processor generate a schedule of at least one protocol to be executed by at least one of the plurality of instruments, wherein:

at least one prerequisite operation is performed in preparation for a protocol execution;

the prerequisite operation prompts a user fora first input; and the processor is configured to substitute a second input using heuristics upon the failure of the user to provide the first input within a predetermined time period.

18. The system of claim 17, wherein the plurality of electrically controllable resources includes resources in the incubator cabinet and/or on the transfer device used by the processor to locate and/or align the transfer device.

19. The system of claim 17, wherein the processor learns by using data from at least one previous protocol run to modify a future protocol run.

20. The system of claim 17, wherein the processor is in communication with and receives machine state data from the database to merge data regarding protocol runs, operational settings, cell line specific settings, and machine state into an executable protocol.

* * * * *